(12) United States Patent
Gu et al.

(10) Patent No.: US 10,317,415 B2
(45) Date of Patent: Jun. 11, 2019

(54) SALIVARY BIOMARKERS FOR MONITORING OF TYPE 2 DIABETES TREATMENT

(71) Applicants: Xinbin Gu, Washington, DC (US); Grace Robinson, Washington, DC (US)

(72) Inventors: Xinbin Gu, Washington, DC (US); Grace Robinson, Washington, DC (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 15/066,941

(22) Filed: Mar. 10, 2016

(65) Prior Publication Data

US 2016/0266148 A1 Sep. 15, 2016

Related U.S. Application Data

(60) Provisional application No. 62/131,207, filed on Mar. 10, 2015.

(51) Int. Cl.
*G01N 33/68* (2006.01)

(52) U.S. Cl.
CPC . *G01N 33/6893* (2013.01); *G01N 2333/4725* (2013.01); *G01N 2333/525* (2013.01); *G01N 2800/042* (2013.01); *G01N 2800/52* (2013.01)

(58) Field of Classification Search
CPC .................................................. G01N 33/6893
See application file for complete search history.

(56) References Cited

U.S. PATENT DOCUMENTS

2015/0119279 A1* 4/2015 Wong .................. C12Q 1/6883
506/9
2015/0301063 A1* 10/2015 Alman ............... G01N 33/6869
506/9

OTHER PUBLICATIONS

Malathi et al., (ISRN Dentistry. Jan. 29, 2014. ArticleID 158786, 8 pages).*
Chan, et al., (Int J Mol Sci. 2012;13:4642-4654).*
Rao et al., (J Proteome Research. Jan. 2, 2009; 8:239-245 (printed with Supplemental Table as a total of 38 pages).*
Gilbert, Amber, et al., "Salivary Biomarkers in African American Type-II Diabetic Patients," Howard University Research Day, Apr. 4, 2014, Abstract Book, p. 20.

* cited by examiner

*Primary Examiner* — Elly-Gerald Stoica
(74) *Attorney, Agent, or Firm* — Fitch, Even, Tabin & Flannery LLP

(57) ABSTRACT

The disclosure relates to the identification of salivary biomarkers for diagnosis and monitoring of type 2 diabetes in a subject. Also provided are methods for noninvasively diagnosing and monitoring type 2 diabetes in a subject. More particularly, the expression of salivary biomarkers, including MUC-1, MUC-2, MUC-4, and MUC-5B, are highly associated with A1C level in African American patients with type 2 diabetes.

20 Claims, 9 Drawing Sheets

FIG. 2B

Western Blot method

ELISA method

Western Blot method 9.0   11.1   A1C (%)

ELISA method

SALIVARY BIOMARKERS FOR MONITORING OF TYPE 2 DIABETES TREATMENT

CROSS REFERENCE TO RELATED APPLICATION

This application claims the benefit of U.S. Provisional Application No. 62/131,207, filed Mar. 10, 2015, which is incorporated herein by reference in its entirety.

FIELD

The disclosure relates to salivary biomarkers, particularly to salivary biomarkers for diagnosing and monitoring the treatment of subjects with Type 2 diabetes.

BACKGROUND

Diabetes mellitus is a great threat to global health. Diabetes affects an estimated 171 million people worldwide. In 2014, the Centers for Disease Control and Prevention ("CDC") estimated that 29.1 million people in the United States have diabetes. The CDC also reports that Type 2 diabetes accounts for 90 to 95 percent of diabetes cases.

Statistics show that diabetes disproportionately affects certain racial/ethnic populations. It has been reported that American Indians, Alaska Natives, African Americans, Hispanics or Latinos, Asian Americans, Native Hawaiians, and other Pacific Islanders have a higher prevalence of diabetes compared to non-Hispanic whites. For instance, the American Diabetes Association reports that 13.2 percent of all African Americans aged 20 years or older are diagnosed with diabetes, while 7.6 percent of non-Hispanic whites are diagnosed with diabetes.

Diabetes can lead to other serious local and systemic complications, including stroke, kidney disease, high blood pressure, ketoacidosis, gastroparesis, hyperosmolar hyperglycemic nonketotic syndrome (HHNS), neuropathy, poor circulation, retinopathy, cataracts, and glaucoma.

Type 2 diabetes can be diagnosed by a variety of conventional tests, including glycated hemoglobin (A1C), random blood sugar, fasting blood sugar, and oral glucose tolerance tests. These diagnostic tests require drawing a blood sample from the patient.

Saliva has recently been found to be a promising bodily fluid for diagnostic purposes. Saliva collection is non-invasive compared to phlebotomy and, as a result, may be more acceptable or convenient to patients. Further, because saliva collection is less invasive than phlebotomy, additional patients may seek diagnostic testing. Advantageously, it has been found that diagnostic tests using saliva can be just as effective as, and often even more effective than, blood-based tests because saliva samples can reflect real-time biomarker levels, unlike other biological fluids, such as urine which is stored in the bladder for a few hours before sampling.

It would be desirable to identify reliable saliva biomarkers for diabetes, particularly type 2 diabetes. Identification of such biomarkers may enable earlier detection of type 2 diabetes and provide more desirable testing options to patients.

SUMMARY

In one approach, the present disclosure provides salivary biomarkers that are useful in the diagnosis of type 2 diabetes, particularly in African American patients. In one particular aspect, these biomarkers include Mucin-1 (MUC-1), Mucin-2 (MUC-2), Mucin-4 (MUC-4), Mucin-5B (MUC-5B), Mucin-7 (MUC-7), TNF-alpha, and Heat shock protein (HSP).

In one embodiment, a method of monitoring the effect of initiating treatment or a change in treatment on diabetes in a subject is provided. The method includes determining a level of at least one of MUC-1, MUC-2, MUC-4, MUC-5B, TNF-alpha, and HSP in a saliva sample obtained from a subject after onset of a treatment or a change in treatment; comparing the subject's level of at least one of MUC-1, MUC-2, MUC-4, MUC-5B, TNF-alpha, and HSP to a predetermined reference value, wherein the predetermined reference value is based on a level of at least one of MUC-1, MUC-2, MUC-4, MUC-5B, TNF-alpha, and HSP in a saliva sample obtained from the subject prior to initiating treatment or change in treatment, and wherein a decreased level of at least one of MUC-1, MUC-4, MUC-5B, TNF-alpha, and HSP or an increased level of MUC-2 in comparison to the predetermined reference value indicates a positive effect of the treatment or change in treatment on the subject's diabetes. In one aspect, the treatment or the change in treatment may include a modification of the subject's diet. In another aspect, the treatment or the change in treatment may include administration of a medication effective to stimulate the pancreas to produce and release more insulin; inhibit the production and release of glucose from the liver; block the action of stomach enzymes that break down carbohydrates; and/or improve the sensitivity of cells to insulin. In yet another aspect, the change in treatment includes adjustment of dosage of a medication effective to stimulate the pancreas to produce and release more insulin; inhibit the production and release of glucose from the liver; block the action of stomach enzymes that break down carbohydrates; and/or improve the sensitivity of cells to insulin. By one exemplary approach, the level of at least one of MUC-1, MUC-2, MUC-4, MUC-5B, TNF-alpha, and HSP is determined by mass spectrometry or ELISA.

In one embodiment, a method of treating type 2 diabetes in a subject having symptoms of or being at risk of developing type 2 diabetes is provided. The method comprises identifying the subject as being in need of treatment for type 2 diabetes by a method comprising measuring the level of at least one of MUC-1, MUC-2, MUC-4, MUC-5B, TNF-alpha, and HSP in a salivary sample from the subject; using the measured level of the at least one biomarker to create a profile for said at least one biomarker; and comparing said profile with a predetermined reference biomarker profile, and finding a deviation of the profile of the sample from the subject with the reference biomarker profile, wherein an upregulation of MUC-1, MUC-4, MUC-5B, TNF-alpha, and HSP, and/or downregulation of MUC-2, identifies the subject as in need of treatment for type 2 diabetes; and effectuating a treatment regimen in the subject.

In another embodiment, a method of treating type 2 diabetes in a subject having symptoms of or being at risk of developing type 2 diabetes is provided. The method comprises (a) detecting the level of at least one type 2 diabetes biomarker in a salivary sample from a subject, wherein detecting comprises contacting the salivary sample with a reagent, wherein the reagent specifically binds at least one salivary biomarker of the group consisting of MUC-1, MUC-2, MUC-4, MUC-5B, TNF-alpha, and HSP; (b) determining that the level of at least one of the type 2 diabetes biomarker in the sample deviates from a predetermined reference value; (c) using the determined deviated level to diagnose type 2 diabetes in the subject; and (d) effectuating a treatment regimen in the subject. In one aspect, the at least one salivary biomarker is selected from the group consisting of MUC-1, MUC-2, MUC-4, and MUC-5B.

In some approaches, the step of determining whether the level of the at least one type 2 diabetes biomarker deviates from the predetermined reference value may comprise the steps of determining the level of at least one type 2 diabetes biomarker in the sample from the subject; and comparing said level to the predetermined reference value.

In a further embodiment, a method of assessing the efficacy of a treatment therapy is provided. The method may include (a) analyzing a first saliva sample from the subject with an assay that specifically detects at least one biomarker selected from MUC-1, MUC-2, MUC-4, MUC-5B, TNF-alpha, and HSP, thereby providing a first biomarker expression profile; (b) effectuating a therapy on the subject; (c) after a treatment period, analyzing a second saliva sample from the subject with an assay that specifically detects at least one biomarker selected from the group consisting of MUC-1, MUC-2, MUC-4, MUC-5B, TNF-alpha, and HSP, thereby providing a second biomarker expression profile; (d) comparing the first and second biomarker expression profiles, thereby assessing the efficacy of the therapy; and (e) optionally effectuating a second therapy on the subject. In one aspect, the at least one salivary biomarker is selected from the group consisting of MUC-1, MUC-2, MUC-4, and MUC-5B.

In some approaches, analyzing the first saliva sample comprises determining the level of at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay. Analyzing the second saliva sample may also comprise determining the level of at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay. In one aspect, analyzing the first saliva sample comprises determining the level of two or more of MUC-1, MUC-2, MUC-4, MUC-5B, TNF-alpha, and HSP. In one aspect, the at least one salivary biomarker is selected from the group consisting of MUC-1, MUC-2, MUC-4, and MUC-5B. In another aspect, analyzing the second saliva sample comprises determining the level of both MUC-2 and MUC-5B.

In yet another embodiment, a method is provided for treating type 2 diabetes in a subject having symptoms of or being at risk of developing type 2 diabetes. The method may comprise (a) determining that a level of at least one type 2 diabetes biomarker selected from the group consisting of MUC-1, MUC-2, MUC-4, MUC-5B, TNF-alpha, and HSP in a salivary sample from a subject deviates from a predetermined reference value of MUC-1, MUC-2, MUC-4, MUC-5B, TNF-alpha, and/or HSP; (b) using the determined deviated level to diagnose type 2 diabetes in the subject; and (c) effectuating a treatment regimen in the subject.

In a further aspect, the various methods described herein may include determining the level of at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay. In some aspects, the at least one type 2 biomarker comprises mRNA, protein, peptide, and/or polypeptide biomarker. In one approach, the level of the at least one type 2 diabetes biomarker is determined by ELISA, Western blot or mass spectroscopy.

BRIEF DESCRIPTION OF THE DRAWINGS

FIG. 2B: Mapping of salivary MUC-2 peptides determined by Mass Spectrometry Analysis.

DETAILED DESCRIPTION

Figures 1A, 1B:
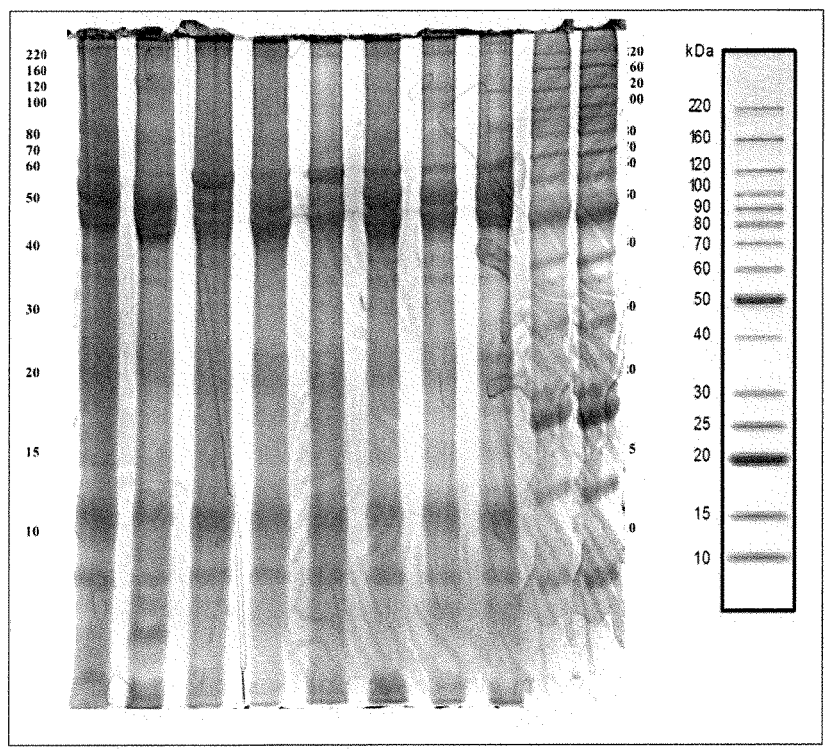
FIG. 1A: A Coomassie blue stained gel.
FIG. 1(B): A table identifying the lanes of the gel in (A).

The methods and biomarkers described herein allow for non-invasive diagnosis, prediction, and monitoring related to prediabetes and type 2 diabetes. Type 2 diabetes is characterized by failure of the body to use insulin properly, which may result in blood glucose levels rising to higher than normal levels (hyperglycemia). Generally the pancreas is unable to produce sufficient insulin to maintain normal blood glucose levels. If left undiagnosed or untreated, type 2 diabetes can lead to a variety of serious health issues.

As described herein, type 2 diabetes may be predicted, monitored, or diagnosed by obtaining a profile of one or more biomarkers from a saliva sample obtained from a subject. For purposes herein, the terms "saliva" or "salivary sample" refer to any watery discharge from the mouth or throat. In another aspect, the biomarker profile may also be used to diagnose prediabetes, which indicates a high risk of developing type 2 diabetes. In another aspect, the biomarker profile associated with type 2 diabetes can be used to improve clinical diagnosis and monitoring of patients already diagnosed with prediabetes or type 2 diabetes.

Advantageously, the methods provided herein can be performed on saliva samples. Saliva is essential for the health of the oral cavity. Saliva is secreted by major and minor salivary glands, including the submandibular gland (SMG), parotid gland (PG) and the sublingual gland (SLG). Saliva contains a complex mixture of proteins with different biological roles in digestion, host defense and lubrication. Salivary immunoglobulins and mucins are believed to be essential in the removal of microorganisms (bacterial aggregation and potential infection) from the oral cavity. The saliva also adds a mucus coat which can protect tooth enamel.

Salivary biomarkers have been identified herein which are associated with type 2 diabetes, particularly in African-Americans with type 2 diabetes. It has been found that several biomarkers—namely, MUC-1, MUC-2, MUC-4, MUC-5B, MUC-7, TNF-alpha, and HSP—can be found in saliva samples and are associated with the incidence of type 2 diabetes. Mucins have important biological functions, including the protection, lubrication, and moisturisation of the surfaces of epithelial tissues within the mouth, pancreas, and other tissues. Deregulated mucin production is a hallmark of inflammatory disorders of the pancreas, and the inflammatory microenvironment affects release of insulin from beta cells in the pancreas. Salivary mucins are heavily glycosylated high-molecular weight glycoproteins produced by submandibular, sublingual and palatal glands and the minor salivary glands in the lip, cheek and tongue. Up to 26 percent of all salivary proteins are mucins. (Zalewska, Acta Biochim Pol. 2000; 47(4):1067-79.) There are two types of mucin that can be found in human saliva-oligomeric mucin glycoprotein (MG1) with molecular mass above 1 MDa and monomeric mucin glycoprotein. (*Acta Biochim Pol*. 2000; 47(4):1067-79.) TNF-alpha and HSP are also related to inflammation. Therefore, these biomarkers can be used as treatment targets to improve the microenvironment, such as of the pancreas, and treatment outcome of type 2 diabetes.

At least in some approaches, the biomarkers disclosed herein can be used in methods to diagnose and/or identify subjects that have, do not have, or are at risk for having prediabetes or type 2 diabetes; to monitor subjects that are undergoing therapies for prediabetes or type 2 diabetes; to determine or suggest a new therapy or a change in therapy for a subject diagnosed with prediabetes or type 2 diabetes; and/or to evaluate the severity or change in severity of prediabetes or type 2 diabetes in a subject. In further approaches, the methods described herein may be used to identify and/or diagnose subjects who are asymptomatic or presymptomatic for type 2 diabetes. In this context, "asymptomatic" or "presymptomatic" means not exhibiting the traditional symptoms of type 2 diabetes, such as but not limited to fatigue, weight loss, blurred vision, increased thirst or frequent urination, increased appetite, and slow wound healing.

As used herein, a "subject" refers to an animal, preferably a mammal, such as, for example, a human or non-human primate. In some aspects, the subject is a human and may be referred to as a patient. A subject may be one who has been previously diagnosed or identified as having prediabetes or type 2 diabetes, and optionally has already undergone or is undergoing a therapeutic intervention for prediabetes or type 2 diabetes. Alternatively, a subject can also be one who has not been previously diagnosed as having prediabetes or type 2 diabetes. For example, a subject can be one who exhibits one or more risk factors for prediabetes or type 2 diabetes. Alternatively, a subject may be one who does not exhibit a risk factor for prediabetes or type 2 diabetes or who is asymptomatic for prediabetes or type 2 diabetes. Risk factors for type 2 diabetes include, for example, weight, family history, sedentary lifestyle, and age.

At least in some approaches, measurements of one or more biomarkers as described herein may lead to a healthcare provider or practitioner to effectuate a therapy with respect to the subject. The terms "therapy" or "treatment" may be used interchangeably and include, for example, initiating therapy, continuing therapy, modifying therapy, or ending therapy. A therapy may also include any prophylactic measures that may be taken to prevent prediabetes or type 2 diabetes.

The diagnosis provided herein may be used to inform the appropriate treatment for prediabetes or type 2 diabetes. At least in some approaches, type 2 diabetes may be managed by increasing exercise and making dietary changes. If blood sugar levels are not adequately lowered by these measures alone, type 2 diabetes is often treated with medication, such as those which (1) stimulate the pancreas to produce and release more insulin; (2) inhibit the production and release of glucose from the liver, (3) block the action of stomach enzymes that break down carbohydrates, and/or (4) improve the sensitivity of cells to insulin. Exemplary medications include but are not limited to metformin, sulfonylureas, meglitinides, thiazolidinediones, DPP-4 inhibitors, GLP-1 receptor agonists, and SGLT2 inhibitors. Insulin therapy may also be used to treat type 2 diabetes.

In some aspects, the medication can be a therapeutic or prophylactic drug used in a subject diagnosed or identified with prediabetes or type 2 diabetes or at risk of having prediabetes or type 2 diabetes. In certain aspects, modifying therapy may refer to altering the duration, frequency or intensity of therapy, such as, for example, altering dosage levels. In other aspects, effectuating a therapy may include causing a subject to or communicating to a subject the need to make a change in lifestyle, for example, increasing exercise and/or changing diet. The therapy may also include surgery.

As used herein, the terms "type 2 diabetes biomarker" or "biomarker" refer to one or more of a gene, mRNA, polypeptide, or protein that is present in a salivary sample from a subject with prediabetes or type 2 diabetes at a different concentration than in a salivary sample of a non-diabetic individual. A biomarker profile refers to one or more, in another aspect two or more, in another aspect three or more, and in another aspect four or more biomarkers. At least in some approaches, while detection of one biomarker may be useful as a diagnostic, detecting at least two, in another aspect at least three, and in another aspect at least four biomarkers may increase the sensitivity and/or specificity of the diagnostic assay.

The present disclosure provides type 2 diabetes salivary biomarkers that have been identified through patient-based studies of salivary proteins that are differentially expressed in patients with type 2 diabetes. In one aspect, these biomarkers comprise proteins or polypeptides that are differentially expressed in an individual suffering from type 2 diabetes as compared to an average value from non-diabetic subjects. In another aspect, these biomarkers comprise nucleic acids that are differentially expressed in an individual suffering from type 2 diabetes as compared to an average value from non-diabetic subjects. In one approach, these biomarkers may include any of MUC-1, MUC-2, MUC-4, MUC-5B, MUC-7, TNF-alpha, and HSP. In one aspect and as shown in the Example herein, type 2 diabetes salivary biomarkers were found at either higher or lower levels in the saliva of type 2 diabetes patients as compared to the saliva of non-diabetic individuals (i.e., control or reference population). For example, MUC-1, MUC-4, MUC-5B, MUC-7, TNF-alpha, and HSP are upregulated in subjects with type 2 diabetes, and MUC-2 is downregulated in subjects with type 2 diabetes in comparison to subjects without type 2 diabetes (reference population).

In the methods provided herein, the level of biomarker expression in a subject suspected to have prediabetes or type 2 diabetes can be compared to a reference biomarker expression profile, such as levels of one or more salivary biomarkers in a salivary sample from one or more non-diabetic individuals, one or more individuals diagnosed with prediabetes, or one or more individuals diagnosed with type 2 diabetes.

In one approach, the biomarker level(s) of the subject may be compared to a predetermined reference value. The predetermined reference value may be an average biomarker value for a control population. The control population can be a group of at least three, in another aspect at least ten, and in another aspect at least 50 people who have a normal A1C level (<5.7).

In another approach, the predetermined reference value may be from the same subject (e.g., person), such that the predetermined reference value was previously obtained by measurement of the saliva of that same subject. This allows for a comparison of a salivary sample from an earlier time period with a salivary sample from a later time period, thereby allowing for evaluation of the efficacy of a treatment or change in treatment. Improvements in the subject can then be directly assessed.

In one embodiment, a method of monitoring the effect of initiating treatment or a change in treatment on diabetes in a subject is provided. The method includes determining a level of at least one of MUC-1, MUC-2, MUC-4, MUC-5B, TNF-alpha, and HSP in a saliva sample obtained from a subject after onset of a treatment or a change in treatment; comparing the subject's level of at least one of MUC-1, MUC-2, MUC-4, MUC-5B, TNF-alpha, and HSP to a predetermined reference value, wherein the predetermined reference value is based on a level of at least one of MUC-1, MUC-2, MUC-4, MUC-5B, TNF-alpha, and HSP in a saliva sample obtained from the subject prior to initiating treatment or change in treatment, and wherein a decreased level of at least one of MUC-1, MUC-4, MUC-5B, TNF-alpha, and HSP or an increased level of MUC-2 in comparison to the predetermined reference value indicates a positive effect of the treatment or change in treatment on the subject's diabetes.

In another embodiment, a method of treating type 2 diabetes in a subject having symptoms of or being at risk of developing type 2 diabetes is provided. The method comprises identifying the subject as being in need of treatment for type 2 diabetes by a method comprising measuring the level of at least one salivary biomarker selected from MUC-1, MUC-2, MUC-4, MUC-5B, TNF-alpha, and HSP in a salivary sample from the subject; using the measured level of the at least one biomarker to create a profile for said at least one biomarker; and comparing said profile with a predetermined reference biomarker profile, and finding a deviation of the profile of the sample from the subject with the reference biomarker profile, wherein an upregulation of MUC-1, MUC-4, MUC-5B, TNF-alpha, and HSP, and/or downregulation of MUC-2, identifies the subject as in need of treatment for type 2 diabetes; and effectuating a treatment regimen in the subject.

In another embodiment, a method of treating type 2 diabetes in a subject having symptoms of or being at risk of developing type 2 diabetes is provided. The method comprises (a) detecting the level of at least one type 2 diabetes biomarker in a salivary sample from a subject, wherein detecting comprises contacting the salivary sample with a reagent, wherein the reagent specifically binds at least one salivary biomarker of the group including MUC-1, MUC-2, MUC-4, MUC-5B, TNF-alpha, and HSP; (b) determining that the level of at least one of the type 2 diabetes biomarker in the sample deviates from a reference value; (c) using the determined deviated level to diagnose type 2 diabetes in the subject; and (d) effectuating a treatment regimen in the subject. For example, the reagent may include an aptamer, photoaptamer, antibody, protein, peptide, peptidomimetic or small molecule. The term "antibody" generally refers to any immunologic binding agent, and the term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. In one aspect, the antibody may be any of IgA, IgD, IgE, IgG and IgM classes. In another aspect, the antibody may be a polyclonal antibody, a monoclonal antibody, or a mixture of monoclonal antibodies. The term "small molecule" refers to compounds with a size comparable to those organic molecules generally used in pharmaceuticals, such as those ranging in size up to about 5000 Da, in another aspect up to about 3000 Da, in another aspect up to 1000 Da.

In some approaches, the step of determining whether the level of the at least one type 2 diabetes biomarker deviates from the reference value may comprise the steps of determining the level of at least one type 2 diabetes biomarker in the sample from the subject; and comparing said level to at least a first reference value.

Advantageously, it has been found that saliva samples are stable when stored at −70° C. Therefore, saliva samples can be taken at various time points, which may assist in monitoring and assessing treatment efficacy. Therefore, in a further embodiment, a method of assessing the efficacy of a treatment therapy on a subject is provided. The method may include (a) analyzing a first saliva sample from the subject with an assay that specifically detects at least one biomarker selected from MUC-1, MUC-2, MUC-4, MUC-5B, TNF-alpha, and HSP, thereby providing a first biomarker expression profile; (b) effectuating a therapy on the subject; (c) after a treatment period, analyzing a second saliva sample from the subject with an assay that specifically detects at least one biomarker selected from the group consisting of MUC-1, MUC-2, MUC-4, MUC-5B, TNF-alpha, and HSP, thereby providing a second biomarker expression profile; (d) comparing the first and second biomarker expression profiles, thereby assessing the efficacy of the therapy; and (e) optionally effectuating a second therapy on the subject. In some approaches, the treatment period may vary between days to weeks, as determined by a medical professional.

In some approaches, analyzing the first saliva sample comprises determining the level of at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay. Analyzing the second saliva sample may also comprise determining the level of at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay. In one aspect, analyzing the first saliva sample comprises determining the level of both MUC-2 and MUC- 5B. In another aspect, analyzing the second saliva sample comprises determining the level of both MUC-2 and MUC-5B.

In yet another embodiment, a method is provided for treating type 2 diabetes in a subject having symptoms of or being at risk of developing type 2 diabetes. The method may comprise (a) determining that a level of at least one type 2 diabetes biomarker selected from the group consisting of MUC-1, MUC-2, MUC-4, MUC-5B, TNF-alpha, and HSP in a salivary sample from a subject deviates from at least one predetermined reference value of MUC-1, MUC-2, MUC-4, MUC-5B, TNF-alpha, and/or HSP; (b) using the determined deviated level to diagnose type 2 diabetes in the subject; and (c) effectuating a treatment regimen in the subject. In some approaches, the levels of both MUC-2 and MUC-5B are determined to deviate from predetermined reference levels of MUC-2 and MUC-5B.

In a further aspect, the various methods described herein may include determining the level of at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay. In some aspects, the at least one type 2 biomarker comprises mRNA, peptide, or polypeptide biomarker. In one approach, the level of the at least one type 2 diabetes biomarker is determined by ELISA, Western blot or mass spectroscopy.

In another aspect, methods are provided for determining the expression level of salivary biomarkers. The methods may include detecting at least one of the biomarkers associated with type 2 diabetes in the saliva of a subject. In another aspect, methods are provided for detecting at least two biomarkers associated with type 2 diabetes in the saliva of a subject. In another aspect, methods are provided for detecting at least three biomarkers associated with type 2 diabetes in the saliva of a subject.

In another aspect, a method is provided for diagnosing type 2 diabetes in an individual, the method comprising: (a) contacting a salivary sample from a subject with a reagent that specifically binds to at least one biomarker; and (b) determining whether or not said at least one biomarker is differentially expressed in the sample. In one embodiment, the at least one biomarker is a protein or nucleic acid that is differentially expressed in the saliva of a subject having type 2 diabetes. In a particular embodiment, the biomarker may be one or more of MUC-1, MUC-2, MUC-4, MUC-5B, MUC-7, TNF-alpha, and HSP. In one approach, determining whether or more biomarkers are differentially expressed may include the steps of (a) determining the level of the at least one biomarker in a sample from the subject; and (b) comparing said level to at a predetermined reference level.

In another aspect, a method is provided for diagnosing type 2 diabetes in an individual, the method including (a) generating a mass spectrometry profile from the saliva of an individual and (b) comparing the mass spectrometry profile to at least a first predetermined reference profile corresponding to a diagnosis of no type 2 diabetes. In a further aspect, the method further comprises comparing the mass spectrometry profile to a second reference profile corresponding to a diagnosis of type 2 diabetes and determining which reference profile best corresponds to the salivary mass spectrometry profile of said individual.

The level of biomarker in an individual suspected to have pre-diabetes or type 2 diabetes, or a comparative individual who does not have diabetes, can be detected by a variety of techniques including, for example, ELISA or other antibody based assay, Western blot, mass spectrometry, microarray, protein microarray, flow cytometry, immunofluorescence, PCR, immunohistochemistry, and multiplex detection assay.

The term "differentially expressed" generally refers to a protein or nucleic acid that is upregulated/overexpressed or downregulated/underexpressed in one biological sample compared to at least one other sample. For example, one or more biomarkers may be upregulated or downregulated in a salivary sample from a subject having prediabetes or type 2 diabetes as compared to an average value from non-diabetic subjects.

As used herein, the terms "upregulate" or "overexpress" or similar term refer to a biomarker that is present at a detectably greater level in a salivary sample from a subject with prediabetes or type 2 diabetes as compared to an average value from non-diabetic subjects. Conversely, the terms "downregulate" or "underexpress" refer to a biomarker that is present at a detectably lower level in a salivary sample from a subject with prediabetes or type 2 diabetes as compared to an average value from non-diabetic subjects.

In several embodiments provided herein, a subject may be diagnosed as having prediabetes or type 2 diabetes when the level of salivary MUC-2 is down-regulated by at least 3 ng/mL as compared to the predetermined reference value. In another aspect, a subject may be diagnosed as having prediabetes or type 2 diabetes when the level of salivary MUC-5B is up-regulated by at least 4 ng/mL as compared to the predetermined reference value. In yet another aspect, a subject may be diagnosed as having prediabetes or type 2 diabetes when the level of salivary MUC-7 is up-regulated by at least 0.8 ng/mL as compared to the predetermined reference value.

In some aspects, upregulation or downregulation may be due to differences in one or more of transcription, post transcriptional processing, translation, post-translational processing, cellular localization, and RNA and protein stability, as compared to a sample from a patient without diabetes. Upregulation or downregulation may be detected using conventional techniques for detecting mRNA (e.g., RT-PCR) or proteins (e.g., Western blot, ELISA, immunohistochemical techniques, or mass spectroscopy). In one aspect, upregulation or downregulation of a biomarker can be at least 10 percent, in another aspect at least 20 percent, in another aspect at least 30 percent, in another aspect at least about 40 percent, in another aspect at least about 50 percent, in another aspect at least about 60 percent, and in another aspect at least about 70 percent higher or lower, respectively, in comparison to a predetermined reference level of the biomarker.

The above aspects and embodiments are further supported by the following non-limiting examples.

Example

Over 2500 proteins and 10,000 peptides were detected from salivary samples by HPLC/MS. As shown in this experiment, the levels of certain glycoproteins, particularly mucin 2, mucin 5B, and mucin 7 proteins (MUC-2, MUC-5B, and MUC-7), were notably different between non-diabetic subjects and those with uncontrolled type 2 diabetes.

Saliva samples were collected from 47 African American patients ranging in age from 26 to 83. Each patient was also analyzed for height, weight and waist circumference to calculate body mass index (BMI). The A1C scores of the patents were also recorded. The patients were then categorized into four groups depending on A1C score: (1) non-diabetic control (AIC score of 4.6-5.7; (2) controlled diabetic (A1C score of 5.8-6.9); (3) uncontrolled diabetic group A (A1C score of 7.0-9.6); and (4) uncontrolled diabetic group B (A1C score of 10.0-16.0).

Dental x-rays and dental examination were also conducted for each patient. Specifically, each patient was evaluated for gingival recession (i.e., measure distance the gum has moved down on the tooth), bleeding on probing or "BOP" (i.e., determine if gum bleeds when manipulated by dental probe), and probing pocket depth or "PPD" (i.e., measure distance dental probe can be introduced under the gum.

The patient groups are summarized below in Table 1.

TABLE 1

| Group | A1C | BMI % | Age | Number of Patients |
|---|---|---|---|---|
| 1 | 4.6-5.7 | 17.7-35.9 | 26-63 | 33 |
| 2 | 5.8-6.9 | 21.1-44.5 | 33-68 | 11 |
| 3 | 7.0-9.6 | 26.9-44.5 | 40-83 | 20 |
| 4 | 10.0-16.0 | 24.4-47.5 | 46-60 | 5 |

Saliva Isolation and Processing

A total of 5 ml of saliva ware collected from each patient. Samples were immediately placed on ice and preserved with 1% sodium azide. Samples were allowed to thaw at room temperature and then centrifuged at 18,000 g for 10 minutes in a centrifuge to remove particulates. The supernatants were placed in tubes and stored at −80° C. before testing.

Mass Spectrometry

Salivary proteins were analyzed to identify potential biomarkers. Salivary samples were analyzed by mass spectrometry analysis to determine the protein profile. Briefly, 40 µl of concentrated saliva were separated by 10% SDS-PAGE (10% tris glycine gel) and stained with Coomassie Blue.

As shown in FIG. 1A, Coomassie Blue staining showed several major bands and several additional minor bands. The lanes of the gel of FIG. 1A are identified in FIG. 1B. Samples were referenced and grouped according to A1C score. The gel strips containing resolved proteins samples were cut into 5 mm sections and the sections corresponding to proteins with molecular weight of 220 kDa and less than 10 kDa were subjected to in-gel reduction, alkylation and then digestion with trypsin. Tryptic peptides obtained from each slice were applied to nano-LC C18 column connected in line to LTQ-XL Orbitrap mass spectrometer and MS/MS analysis was conducted. Protein mass and retention time were recorded in minutes based on the HPLC gradient curve. MS HPLC was optimized based on the gradient curve and ability to recognize many proteins and peptides.

Figure 2A:
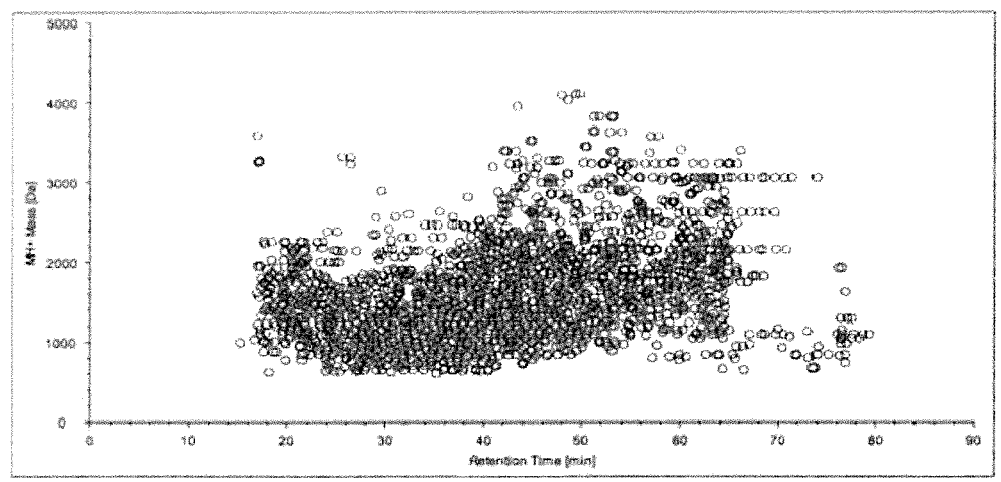
FIG. 2A: A scatter plot of protein mass versus retention time.
Figure 2B:
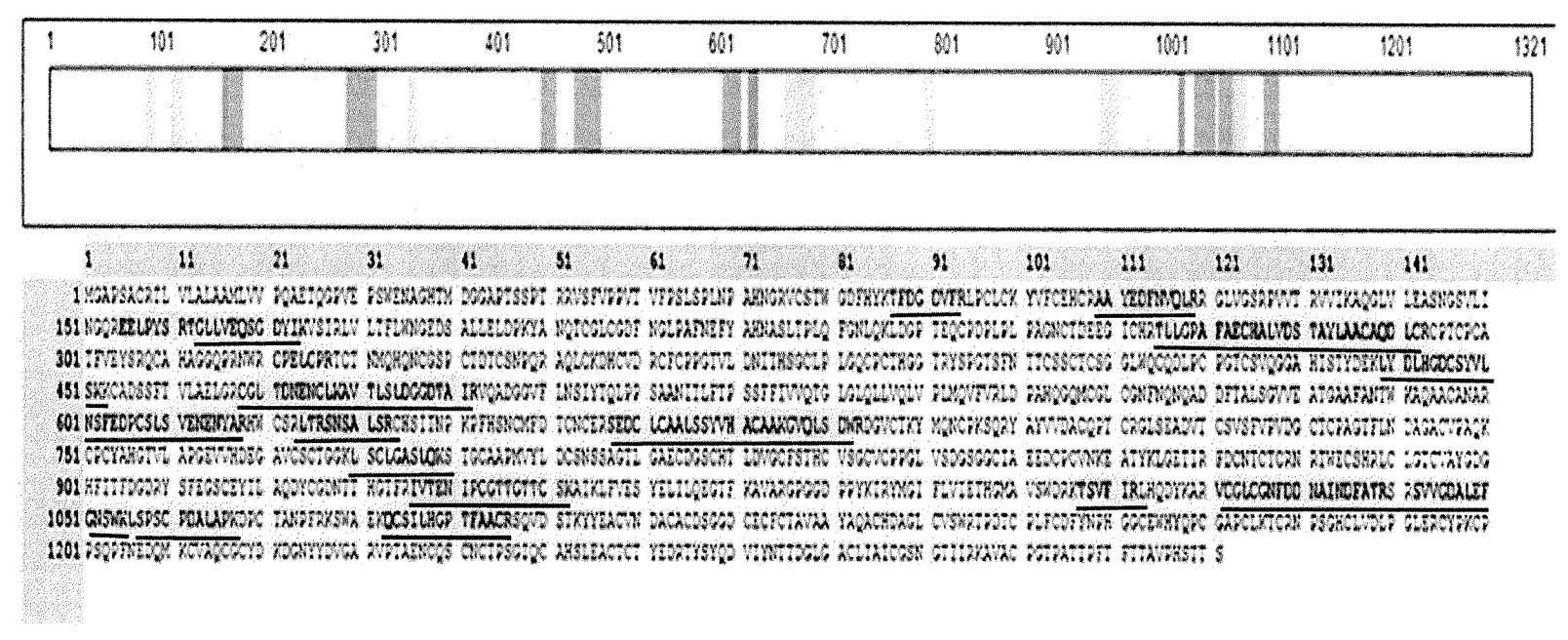
Figure 2C:
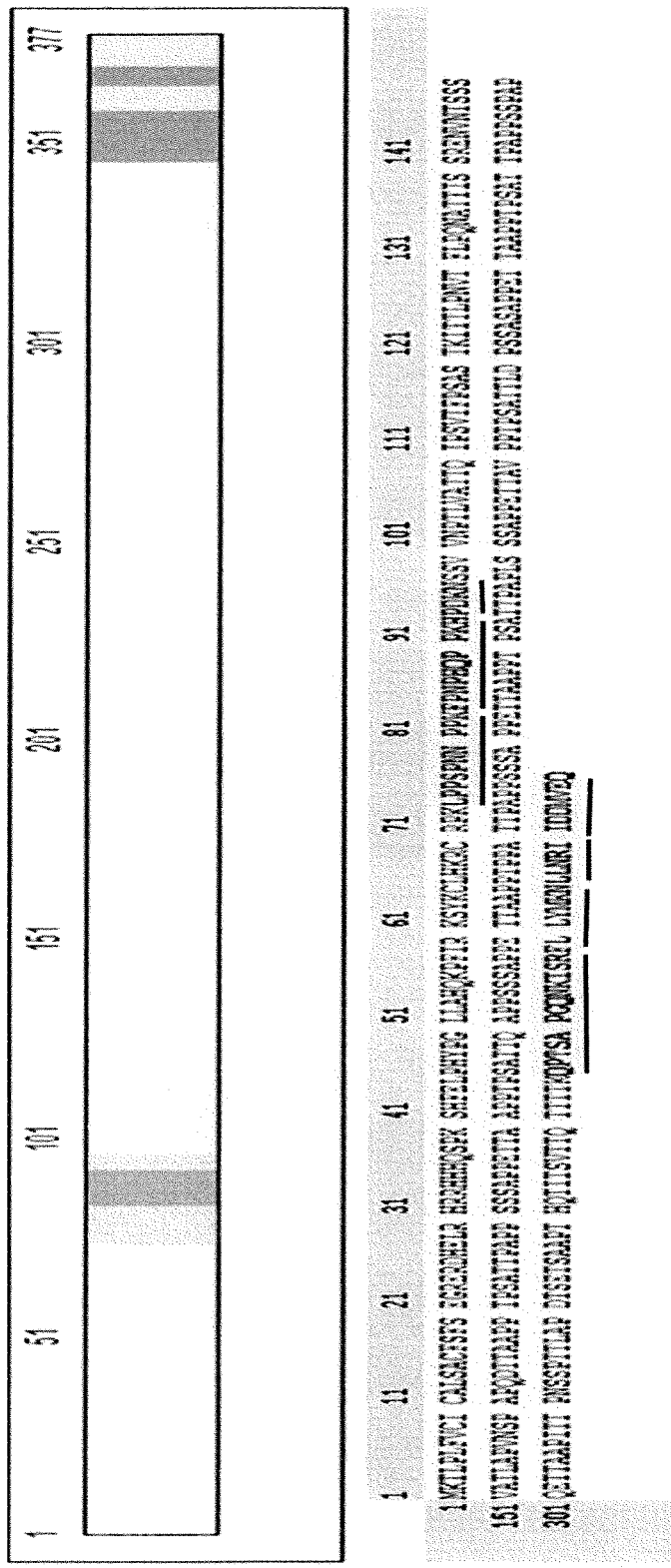
FIG. 2C: Mapping of salivary MUC-7 peptides determined by Mass Spectrometry Analysis.
Figure 2D:
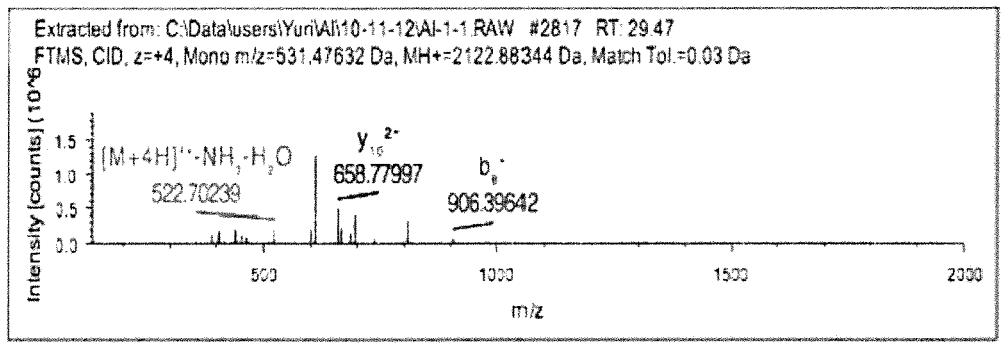
FIG. 2D: Mass spectrometry results for the non-diabetic control patient group.
Figure 2E:
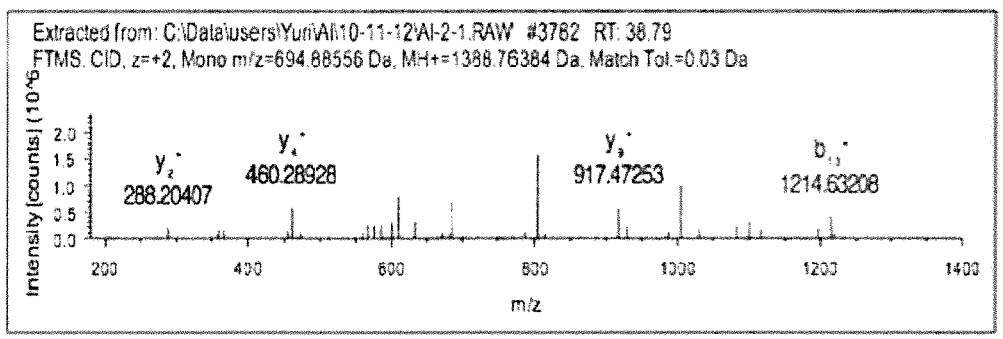
FIG. 2E: Mass spectrometry results for the controlled diabetic patient group.

The results are shown in FIGS. 2A and 2B. Over 10,000 proteins were detected in saliva samples from the controlled diabetic and non-diabetic control groups. Protein mass and retention time were recorded in minutes based on the HPLC gradient curve. FIG. 2A shows a scatter plot of protein mass versus retention time. FIG. 2B shows the mapping of salivary MUC-2 peptides determined by mass spectrometry analysis, and FIG. 2C shows the mapping of salivary MUC-7 peptides determined by mass spectrometry analysis. FIG. 2D shows the mass spectrometry results for the non-diabetic control group. FIG. 2E shows the mass spectrometry results for the controlled diabetic group.

Sequential database searches were performed using human FASTA database (released Aug. 18, 2003). This protein database has a total of 199808 entries and 60322667 residues. Only peptides having cross-correlation (XCorr) cutoffs of 2.6 for $[M+2H]2^+$, 3.0 for $[M+3H]3^+$ and higher charge state were considered. These SEQUEST criteria thresholds resulted in a 1-2% of False Discovery Rate. FDR is determined by search on a decoy database. The proteome analysis of the spectra was made by Proteome Discoverer 1.2 software (Thermo Fisher Scientific).

Western Blot Analysis and ELISA Analysis

Candidate proteins were selected from the above process and further analyzed by Western blot and ELISA.

Antibodies used in this study included those against Muc-2, Muc-5B, and Muc-7 from Santa Cruz (Santa Cruz, Calif.), and those against TNF-alpha, Heat Shock protein, and β-actin from Sigma (St. Louis, Mo.). ELISA kit for Human Mucin 2, Human Mucin 5B, and Human Mucin 7 were obtained from My BioSource (Wuhan, China) and concentrate filter was obtained from EMD Millipore (Taunton, Mass.).

Protein from the saliva samples were quantified using a Bio-Rad protein assay. Proteins of saliva were lysed in SDS-loading buffer, resolved by SDS-PAGE on a 8% Tris-glycine gel, transferred to polyvinylidene fluoride (PVDF) membranes (Bio-Rad), and then probed with the indicated primary antibodies overnight at 4° C. Washed blots were then incubated with horseradish peroxidase-conjugated anti-mouse, or anti-rabbit antibody (Santa Cruz Biotechnology), respectively, for one hour at room temperature. Blots were developed using the peroxidase reaction and visualized with ECL detection system (Bio-Rad).

Figure 3A:
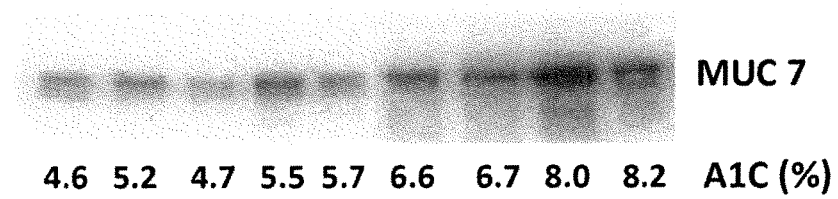
FIG. 3A: Western blot analysis of mucin-7 in salivary samples.
Figure 3B:
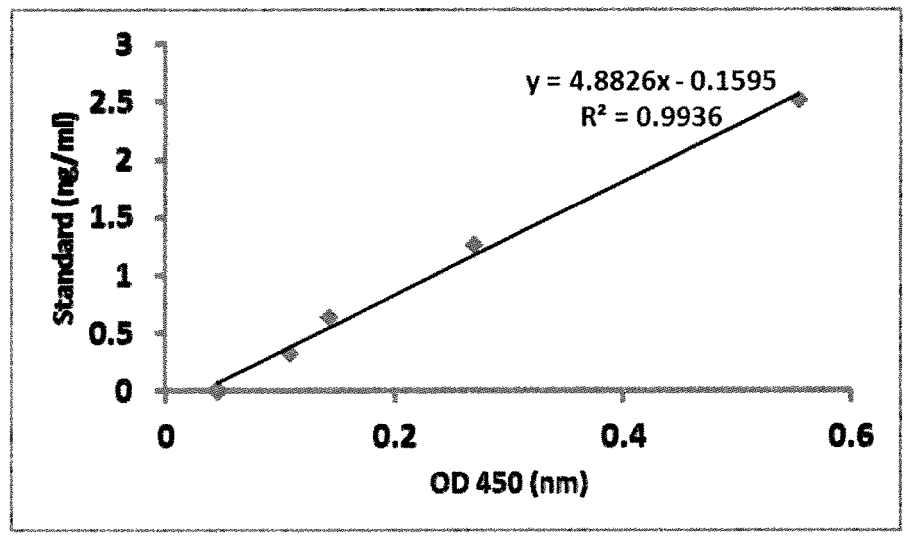
FIG. 3B: MUC-7 standard for ELISA method.
Figure 3C:
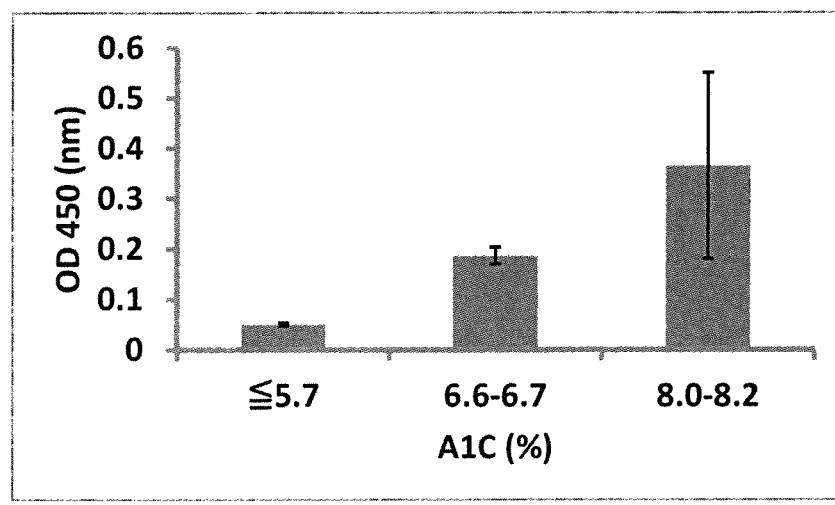
FIG. 3C: Salivary MUC-7 level analyzed by ELISA method.

The Western blot results and ELISA results are shown in FIGS. 3A, 3B, 3C, 4A, and 4B, and the membranes were probed for salivary MUC-7. FIG. 3A, lanes 1 to 9 include samples from A1C 4.6 to 8.2 subjects. FIG. 3B shows a MUC-7 concentration standard curve for ELISA analysis. FIG. 3C shows MUC-7 levels quantified by ELISA analysis.

Figure 4A:
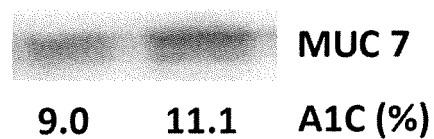
FIG. 4A: Western blot analysis of MUC-7 in salivary samples. The salivary samples were collected in 2013 and stored in −70° C.
Figure 4B:
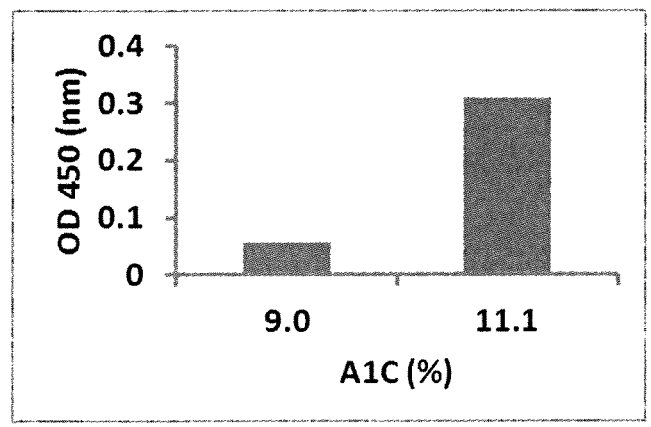
FIG. 4B: ELISA analysis of MUC-7 in salivary samples.

In FIG. 4A, the membranes were probed for Actin, MUC-2, and MUC-7. Lane 1 includes a sample from a non-diabetic control, lanes 2 and 3 include samples from controlled diabetic patients, and lanes 4 and 5 include samples from uncontrolled diabetic patents.

It was found that various protein expression levels differed between type 2 diabetic patients and non-diabetic patients. As shown by Western blot, MUC-7 level was upregulated (as quantified by ELISA method), which was correlated with increased A1C score. The MUC-7 level was significantly higher in the uncontrolled diabetic group compared to the control group. In contrast, the level of MUC-2 was down-regulated in the uncontrolled group with higher A1C score.

Therefore, it was found that the expression of MUC-7 and MUC-2 salivary biomarkers is highly associated with A1C score in African American patients with type-II diabetes, but with MUC-2 levels being inversely correlated to A1C score. In other words, the level of MUC-2 went down with increased A1C score, whereas the level of MUC-7 increased with increased A1C score.

Candidate proteins MUC-2 and MUC-7 were analyzed using indirect ELISA. After appropriate dilution, samples were coated onto assay plates at room temperature and incubated for 2 hours. Standards and sample dilution were provided by Human Muc-2 ELISA kit from My Biosource (Wuhan, China). Results were expressed as absorbances at 450 nm. Standards were sequentially diluted and used to generate standard curves. The curves showed a linear relationship between the gradually diluted standards. The amounts of the proteins in the samples were determined by plotting the optical density with the separate standard curves.

Figure 5:
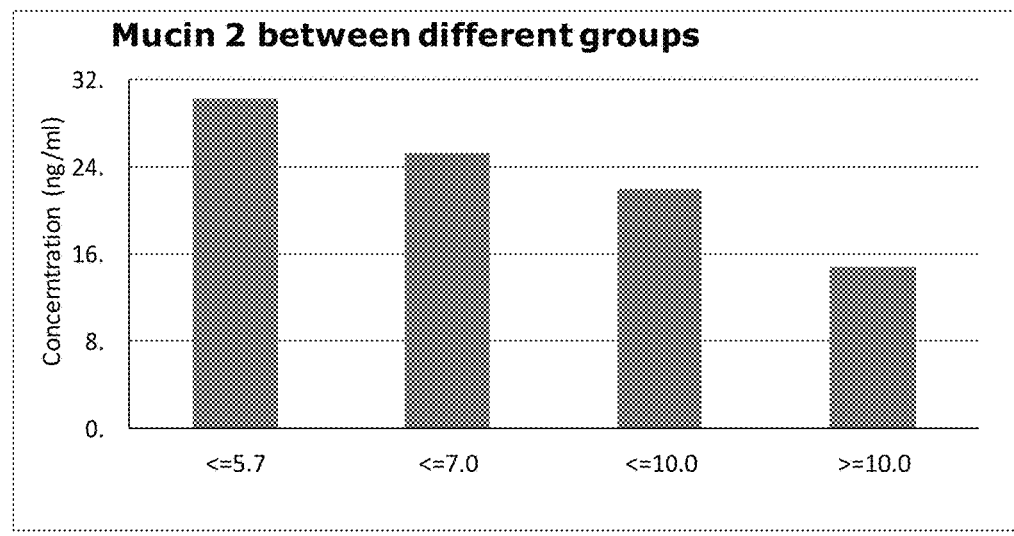
FIG. 5: Representation of ELISA test results showing the amount of MUC-2 in salivary samples.
Figure 6:
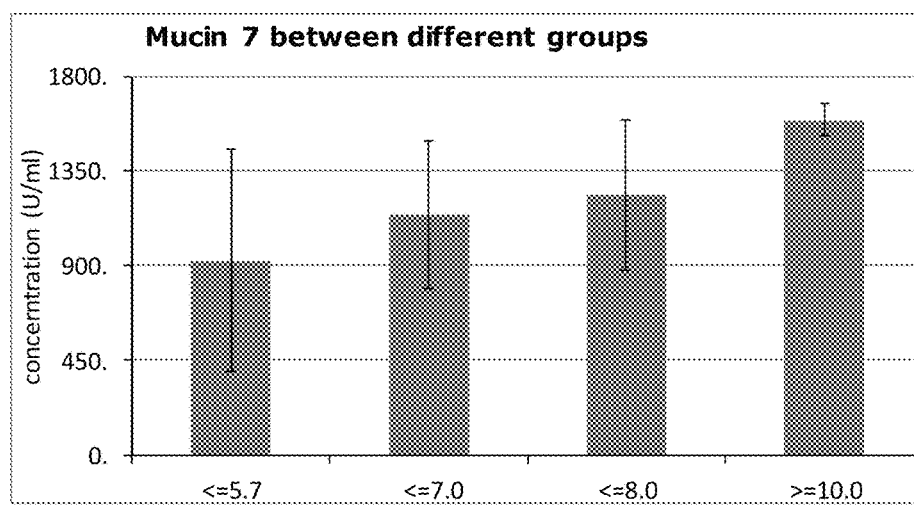
FIG. 6: Representation of ELISA test results showing the amount of MUC-7 in salivary samples.

FIGS. 5 and 6 include bar graphs showing the MUC-2 and MUC-7 levels, respectively, between the four groups of patients. FIGS. 5 and 6 show that MUC-2 is downregulated and MUC-7 is upregulated in uncontrolled diabetic subjects as compared to non-diabetic and controlled diabetic subjects.

Statistical Analyses

Statistical analysis was performed by statistical analysis software SPSS 17.0 using Two-Way Analysis of Variance followed by Student-Newman-Keuls for multiple comparisons. A p value of less than 0.05 was considered significant.

Several publications are referenced in this application. The disclosure of each of these publications is fully incorporated by reference herein.

While certain of the preferred embodiments have been described and specifically exemplified above, it is not intended that the invention be limited to such embodiments. Various modifications may be made thereto without departing from the scope and spirit of the present invention, as set forth in the claims presented hereafter.

What is claimed is:

1. A noninvasive method of monitoring the effect of initiating treatment or a change in treatment on diabetes in a subject having symptoms of or diagnosed as being at risk of developing type 2 diabetes, comprising:
    obtaining a saliva sample from the subject prior to a treatment or a change in treatment;
    determining a level of MUC-2 and a level of at least one of MUC-1, MUC-4, MUC-5B, TNF-alpha, and HSP in the saliva sample obtained from a subject to provide predetermined reference values;
    for a first treatment period, administering a treatment to the subject a medication effective to stimulate the pancreas to produce and release more insulin; inhibit the production and release of glucose from the liver; block the action of stomach enzymes that break down carbohydrates; and/or improve the sensitivity of cells to insulin;
    determining a level of MUC-2 and a level of at least one of MUC-1, MUC-4, MUC-5B, TNF-alpha, and HSP in a saliva sample obtained from a subject after onset of the treatment or the change in treatment;
    comparing the subject's level of MUC-2 and level of at least one of MUC-1, MUC-4, MUC-5B, TNF-alpha, and HSP to the predetermined reference values, wherein a decreased level of at least one of MUC-1, MUC-4, MUC-5B, TNF-alpha, and HSP and an increased level of MUC-2 in comparison to the predetermined reference values indicates a positive effect of the treatment or change in treatment on the subject's diabetes; and
    continuing the treatment for a second treatment period.

2. The method according to claim 1, wherein the change in treatment includes adjustment of dosage of a medication effective to stimulate the pancreas to produce and release more insulin; inhibit the production and release of glucose from the liver; block the action of stomach enzymes that break down carbohydrates; and/or improve the sensitivity of cells to insulin.

3. The method according to claim 1, wherein the levels of MUC-2 and at least one of MUC-1, MUC-4, and MUC-5B and the predetermined reference value are determined by at least one of mass spectrometry.

4. The method according to claim 1, wherein the levels of MUC-2 and at least one of MUC-1, MUC-4, and MUC-5B and the predetermined reference value are determined by ELISA.

5. A method of treating type 2 diabetes in a subject having symptoms of or diagnosed as being at risk of developing type 2 diabetes, the method comprising:
    obtaining a saliva sample from the subject;
    identifying the subject as being in need of treatment for type 2 diabetes by a method comprising:
        measuring the level of MUC-2 and level of at least one salivary biomarker from the group consisting of MUC-1, MUC-4, MUC-5B, TNF-alpha, and HSP in the saliva sample from the subject;
        using the measured level of MUC-2 and level of the at least one biomarker to create a profile for MUC-2 and said at least one biomarker; and
        comparing said profile with a predetermined reference biomarker profile obtained from a subject that does not have type 2 diabetes, and finding a deviation of the profile of the sample from the subject with the predetermined reference biomarker profile, wherein an upregulation of MUC-1, MUC-4, MUC-5B, TNF-alpha, and HSP, and downregulation of MUC-2, identifies the subject as in need of treatment for type 2 diabetes; and
    effectuating a treatment regimen in the subject for a treatment period, wherein the treatment regimen includes one or more medications effective to (1) stimulate the pancreas to produce and release more insulin; (2) inhibit the production and release of glucose from the liver; (3) block the action of stomach enzymes that break down carbohydrates; (4) improve the sensitivity of cells to insulin; or a combination of any of (1) to (4).

6. A method of treating type 2 diabetes in a subject having symptoms of or diagnosed as being at risk of developing type 2 diabetes, the method comprising:
    (a) detecting the levels of MUC-2 and at least one type 2 diabetes biomarker selected from MUC-1, MUC-4, MUC-5B, TNF-alpha, and HSP in a salivary sample from a subject, wherein detecting comprises contacting the salivary sample with at least one reagent, wherein the at least one reagent specifically binds MUC-2 and at least one salivary biomarker of the group including MUC-1, MUC-4, MUC-5B, TNF-alpha, and HSP;
    (b) determining that the levels of MUC-2 and at least one of the type 2 diabetes biomarker in the sample deviates from predetermined reference values;
    (c) using the determined deviated levels to diagnose type 2 diabetes in the subject when the level of MUC-2 is downregulated and the level of one or more of MUC-1, MUC-4, MUC-5B, TNF-alpha, and HSP is upregulated compared to the predetermined reference values; and
    (d) effectuating a treatment regimen in the subject, wherein the treatment regimen includes one or more medications effective to (1) stimulate the pancreas to produce and release more insulin; (2) inhibit the production and release of glucose from the liver; (3) block the action of stomach enzymes that break down carbohydrates; (4) improve the sensitivity of cells to insulin; or a combination of any of (1) to (4).

7. The method claim 6, wherein the method comprises determining the levels of MUC-2 and the at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay.

8. The method of claim 6, wherein the levels of MUC-2 and the at least one type 2 diabetes biomarker is determined by at least one of ELISA and mass spectroscopy.

9. The method of claim 6, wherein the step of determining whether the levels of MUC-2 and the at least one type 2 diabetes biomarker deviates from the predetermined reference values comprises the steps of:
   determining the levels of MUC-2 and the at least one type 2 diabetes biomarker in the sample from the subject; and
   comparing said levels to the predetermined reference levels.

10. A method of assessing the efficacy of a treatment therapy on a subject having symptoms of or diagnosed as being at risk of developing type 2 diabetes, the method comprising:
   (a) analyzing a first saliva sample from the subject with an assay that specifically detects MUC-2 and at least one biomarker selected from MUC-1, MUC-4, MUC-5B, TNF-alpha, and HSP, thereby providing a first biomarker expression profile;
   (b) effectuating a therapy on the subject, wherein the therapy includes one or more medications effective to (1) stimulate the pancreas to produce and release more insulin; (2) inhibit the production and release of glucose from the liver; (3) block the action of stomach enzymes that break down carbohydrates; (4) improve the sensitivity of cells to insulin; or a combination of any of (1) to (4);
   (c) after a treatment period, analyzing a second saliva sample from the subject with an assay that specifically detects MUC-2 and at least one biomarker selected from the group consisting of MUC-1, MUC-4, MUC-5B, TNF-alpha, and HSP, thereby providing a second biomarker expression profile;
   (d) comparing the first and second biomarker expression profiles, thereby assessing the efficacy of the therapy, wherein a decreased level of at least one of MUC-1, MUC-4, MUC-5B, TNF-alpha, and HSP and an increased level of MUC-2 in the second biomarker expression profile in comparison to the first biomarker expression profile indicates a positive effect of the treatment or change in treatment on the subject's diabetes; and
   (e) optionally, after assessing the efficacy of the therapy, effectuating a second therapy on the subject, wherein the second therapy includes one or more medications effective to (1) stimulate the pancreas to produce and release more insulin; (2) inhibit the production and release of glucose from the liver; (3) block the action of stomach enzymes that break down carbohydrates; (4) improve the sensitivity of cells to insulin; or a combination of any of (1) to (4).

11. The method of claim 10, wherein analyzing the first saliva sample comprises determining the levels of MUC-2 and at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay.

12. The method of claim 10, wherein analyzing the second saliva sample comprises determining the levels of MUC-2 and at least one type 2 diabetes biomarker by a method selected from the group consisting of an antibody based assay, ELISA, western blotting, mass spectrometry, micro array, protein microarray, flow cytometry, immunofluorescence, PCR, immunohistochemistry, and a multiplex detection assay.

13. The method of claim 10, wherein the at least one type 2 biomarker comprises a mRNA biomarker.

14. The method of claim 10, wherein the at least one type 2 biomarker comprises a polypeptide biomarker.

15. The method of claim 10, wherein the level of the at least one type 2 diabetes biomarker is determined by ELISA.

16. The method of claim 10, wherein the level of the at least one type 2 diabetes biomarker is determined by mass spectroscopy.

17. The method of claim 10, wherein analyzing the first saliva sample comprises determining the levels of both MUC-2 and MUC-5B.

18. The method of claim 10, wherein analyzing the second saliva sample comprises determining the levels of both MUC-2 and MUC-5B.

19. A method of treating type 2 diabetes in a subject having symptoms of or diagnosed as being at risk of developing type 2 diabetes, the method comprising:
   (a) determining that a level of MUC-2 and a level of at least one type 2 diabetes biomarker selected from the group consisting of MUC-1, MUC-4, MUC-5B, TNF-alpha, and HSP in a salivary sample from the subject deviates from a predetermined reference value;
   (b) using the determined deviated levels to diagnose type 2 diabetes in the subject; and
   (c) effectuating a treatment regimen in the subject, wherein the treatment regimen includes one or more medications effective to (1) stimulate the pancreas to produce and release more insulin; (2) inhibit the production and release of glucose from the liver; (3) block the action of stomach enzymes that break down carbohydrates; (4) improve the sensitivity of cells to insulin; or a combination of any of (1) to (4).

20. The method of claim 19, wherein the level of salivary MUC-2 is down-regulated by at least 3 ng/mL as compared to the predetermined reference value; and
   the level of salivary MUC-5B is up-regulated by at least 4 ng/mL as compared to the predetermined reference value.

* * * * *